United States Patent [19]

Becker et al.

[11] Patent Number: 4,618,362
[45] Date of Patent: Oct. 21, 1986

[54] INCREASING THE SUGAR CONTENT OF PLANTS

[75] Inventors: Rainer Becker, Bad Durkheim; Dieter Jahn, Edingen-Neckarhausen; Ulrich Schirmer, Heidelberg; Eberhard P. Schott, Neustadt; Bernhard Hesse, Neuhofen; Johann Jung, Limburgerhof, all of Fed. Rep. of Germany

[73] Assignee: BASF Aktiengesellschaft, Ludwigshafen, Fed. Rep. of Germany

[21] Appl. No.: 760,042

[22] Filed: Jul. 29, 1985

[30] Foreign Application Priority Data

Aug. 2, 1984 [DE] Fed. Rep. of Germany ....... 3428457

[51] Int. Cl.$^4$ ..................... A01N 43/16; A01N 43/18
[52] U.S. Cl. ............................. 71/88; 71/76; 71/90; 71/106; 71/121
[58] Field of Search .................... 71/76, 88, 90

[56] References Cited

U.S. PATENT DOCUMENTS 4,334,913  6/1982  Koerwer ................................. 71/98
4,351,666  7/1982  Koerwer ................................ 71/106

FOREIGN PATENT DOCUMENTS 0047972  3/1982  European Pat. Off. .

Primary Examiner—Catherine L. Mills
Attorney, Agent, or Firm—Keil & Weinkauf

[57] ABSTRACT

The sugar content of plants is increased by a method in which the plants are treated, from 1 to 15 weeks prior to harvesting, with a compound of the formula (I)

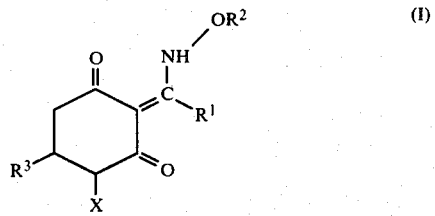

where $R^1$ is alkyl of 1 to 4 carbon atoms, $R^2$ is alkyl of 1 to 4 carbon atoms, unsubstituted or halogen-substituted alkenyl of 3 to 5 carbon atoms or alkynyl of not more than 5 carbon atoms, $R^3$ is a non-aromatic heterocyclic structure which has 5 to 7 ring members and no double bonds or one double bond in a heterocyclic ring, contains 1 or 2 hetero atoms from the group consisting of sulfur and oxygen, and can be substituted by alkyl of not more than 3 carbon atoms, and X is H or C00-alkyl, or one of its plant-tolerated salts.

8 Claims, No Drawings

INCREASING THE SUGAR CONTENT OF PLANTS

The present invention relates to a method for increasing the sugar content of plants by treating them with a cyclohexane-1,3-dione derivative.

It has been disclosed that substituted cyclohexane-1,3-dione derivatives, possess herbicidal properties (German Laid-Open Applications Nos. DOS 2,439,104 and DOS 2,822,304 and European Pat. No. 71,707). Moreover, the herbicidal action is directed in particular against gramineous weeds, while many broad-leaved crops are not damaged.

It has also been disclosed that certain cyclohexanedione derivatives are capable of increasing the sugar content of various plants (European Pat. No. 47,972 and U.S. Pat. No. 4,334,913).

We have found that the sugar content of sugar cane or sweet sorghum can be reliably increased using a very small amount of active ingredient if the plants are treated, from 1 to 15 weeks prior to harvesting, with a compound of the formula (I)

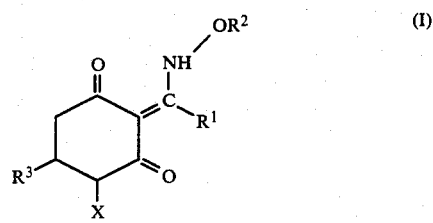

where $R^1$ is alkyl of 1 to 4 carbon atoms, $R^2$ is alkyl of 1 to 4 carbon atoms, unsubstituted or halogen-substituted alkenyl of 3 to 5 carbon atoms or alkynyl of not more than 5 carbon atoms, $R^3$ is a non-aromatic heterocyclic structure which has 5 to 7 ring members and no double bonds or one double bond in the heterocyclic ring, contains one or two hetero atoms from the group consisting of sulfur and oxygen and may be substituted by alkyl of not more than 3 carbon atoms, and X is H or COO-alkyl, or one of its plant-tolerated salts.

$R^1$ is, for example, ethyl or propyl, $R^2$ is, for example, ethyl, allyl, chloroallyl, trichloroallyl, propargyl or propyl, $R^3$ is, for example, tetrahydropyran-3-yl, 4-methyltetrahydropyran-3-yl, dihydropyran-3-yl, tetrahydrothiopyran-3-yl, dihydrothiopyran-3-yl, 1,4-dioxanyl or tetrahydropyran-4-yl, and X is, for example, methoxycarbonyl.

A plant-tolerated salt is, for example, an ammonium or alkali metal (sodium or potassium) salt.

The active ingredients used according to the invention can occur in a number of tautomeric forms, all of which are embraced by formula I:

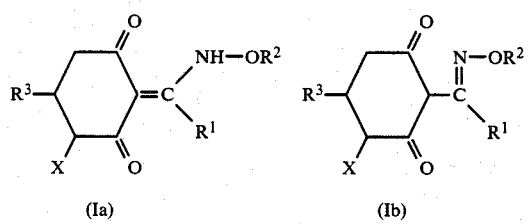

(Ia)    (Ib)

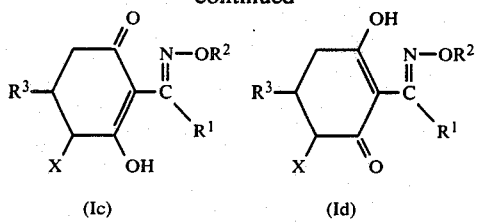

(Ic)    (Id)

The active ingredients can be obtained by reacting a compound of the formula

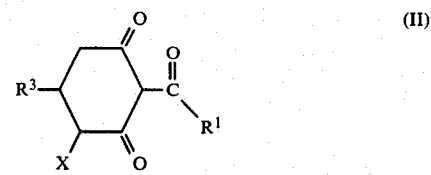

(II)

where $R^1$, $R^3$ and X have the above meanings, with a hydroxylamine derivative $R^2O$—$NH_3Y$, where $R^2$ has the above meanings and Y is an anion.

The reaction is advantageously carried out in a heterogeneous phase in an inert diluent at from from 0° to 80° C., or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. It is also possible to use organic bases, such as pyridine or tertiary amines.

The reaction proceeds particularly well at a pH of 2 to 7, in particular from 4.5 to 5.5, the pH advantageously being established by adding an acetate, for example an alkali metal acetate, in particular sodium acetate or potassium acetate, or a mixture of the two salts. Alkali metal acetates are added in amounts of, for example, from 0.5 to 2 moles, based on the ammonium compound $R^2O$—$NH_3Y$.

Examples of suitable solvents are dimethyl sulfoxide, alcohols, such as methanol, ethanol or isopropanol, benzene, chlorohydrocarbons, such as chloroform or dichloroethane, esters, such as ethyl acetate, and ethers, such as dioxane or tetrahydrofuran.

The reaction is complete after a few hours, and the product can then be isolated by evaporating down the mixture, adding water and extracting with unpolar solvent, such as methylene chloride, and distilling off the solvent under reduced pressure.

The active ingredients may furthermore be obtained by reacting the compound of the formula II with the hydroxylamine of the formula $R^2O$—$NH_2$, while $R^2$ has the above meanings, in an inert diluent at from 0° C. to the boiling point of the reaction mixture, in particular from 15° to 70° C.

Examples of suitable solvents for this reaction are alcohols, such as methanol, ethanol, isopropanol or cyclohexanol, hydrocarbons or chlorohydrocarbons, such as methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating the compounds with sodium hydroxide or potassium hydroxide in aqueous solution or in an organic solvent, such as methanol, ethanol or acetone. Sodium alcoholates and potassium alcoholates can also serve as bases.

The other metal salts, e.g. the manganese, copper, zinc, iron and barium salts, can be prepared from the sodium salts by reaction with the corresponding metal chloride in aqueous solution.

The compounds of the formula II can be prepared, using methods known from the literature (Tetrahedron Lett. 29 (1975), 2491), from cyclohexane-1,3-diones of the formula III, which may also occur in the tautomeric forms of formulae IIIa and IIIb

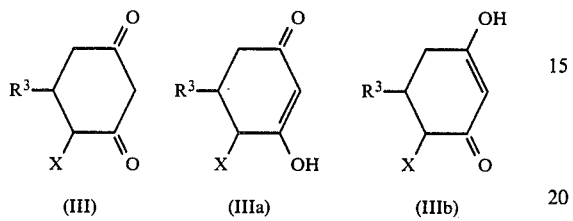

(III)   (IIIa)   (IIIb)

It is also possible to prepare compounds of the formula II via the enol-ester intermediates, which may be obtained as isomer mixtures in the reaction of compounds of the formula III and undergo rearrangement in the presence of imidazole or pyridine derivatives (Japanese Preliminary Publication No. 54/063052).

The compounds of the formula III are obtained by processes known from the literature, as can be seen from the scheme below:

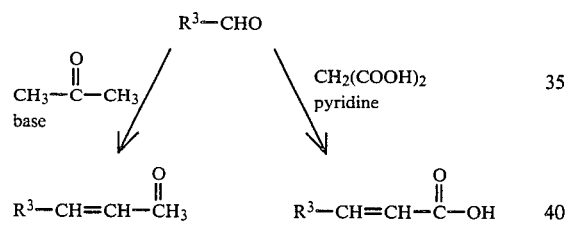

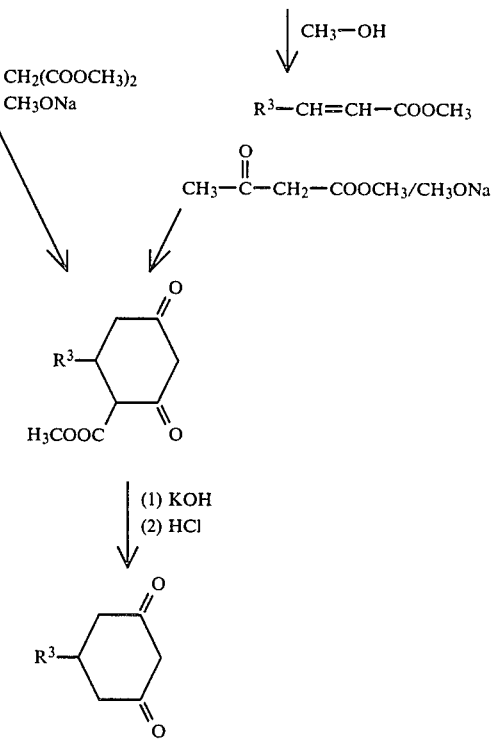

The Example which follows illustrates the method of preparation of the active ingredients.

EXAMPLE 3.69 parts by weight of sodium acetate and 3.51 parts by weight of ethoxyammonium chloride were added to 10.0 parts by weight of 2-butyryl-5-(4-methyltetrahydropyran-3-yl)-cyclohexane-1,3-dione in 100 ml of ethanol, and the mixture was stirred for 20 hours at room temperature. To work up the mixture, it was poured into ice water and extracted with methylene chloride, and the organic phase was washed with water, dried and evaporated down to give 10.7 parts by weight of 2-(1-ethoxyaminobutylidene)-5-(4-methyltetrahydropyran-3-yl)-cyclohexane-1,3-dione (active ingredient No. 1); $n_D^{22} = 1.5235$.

$C_{18}H_{29}NO_4$ (molecular weight=323).

The compounds below (List 1) were prepared in a similar manner:

| No. | $R^1$ | $R^2$ | $R^3$ | X | $^1$H—NMR data/$n_D$/mp. [°C.] |
|---|---|---|---|---|---|
| 2 | Ethyl | Ethyl | 3-Tetrahydrothiopyranyl | H | $n_D^{25} = 1.5540$ |
| 3 | Ethyl | Allyl | 3-Tetrahydrothiopyranyl | H | $n_D^{25} = 1.5644$ |
| 4 | n-Propyl | Ethyl | 3-Tetrahydrothiopyranyl | H | $n_D^{25} = 1.5588$ |
| 5 | n-Propyl | Allyl | 3-Tetrahydrothiopyranyl | H | $n_D^{25} = 1.5559$ |
| 6 | n-Propyl | 3-Chloroallyl (trans) | 3-Tetrahydrothiopyranyl | H | $n_D^{22} = 1.5569$ |
| 7 | n-Propyl | Ethyl | 3-Tetrahydropyranyl | H | $n_D^{24} = 1.5149$ |
| 8 | n-Propyl | Allyl | 3-Tetrahydropyranyl | H | $n_D^{18} = 1.5313$ |
| 9 | Ethyl | Ethyl | 3-Tetrahydropyranyl | H | mp.: 38-40° C. |
| 10 | Ethyl | Allyl | 3-Tetrahydropyranyl | H | $n_D^{18} = 1.5342$ |
| 11 | n-Propyl | Ethyl | 4-Tetrahydropyranyl | H | mp.: 48-50° C. |
| 12 | n-Propyl | Allyl | 4-Tetrahydropyranyl | H | mp.: 55-56° C. |
| 13 | Ethyl | Ethyl | 4-Tetrahydropyranyl | H | δ = 1.35(t), 1.68(d), 3.35(t) |

-continued

| No. | $R^1$ | $R^2$ | $R^3$ | X | $^1$H—NMR data/$n_D$/mp. [°C.] |
|---|---|---|---|---|---|
| 14 | Ethyl | Allyl | 4-Tetrahydropyranyl | H | $\delta$ = 1.15(t), 2.95(g), 3.35(t), 4.50(d) |
| 15 | n-Propyl | Ethyl | 3-Tetrahydrofuranyl | H | mp.: 36–39° C. |
| 16 | n-Propyl | Allyl | 3-Tetrahydropyranyl | H | $n_D^{29}$ = 1.5302 |
| 17 | n-Propyl | Ethyl | 1,4-Dioxanyl | H | $n_D^{22}$ = 1.5226 |
| 18 | n-Propyl | Allyl | 1,4-Dioxanyl | H | $n_D^{22}$ = 1.5229 |
| 19 | n-Propyl | 3- | 1,4-Dioxanyl | H | $n_D^{22}$ = 1.5391 |
| 20 | Ethyl | Ethyl | 1,4-Dioxanyl | H | $n_D^{21}$ = 1.5259 |
| 21 | Ethyl | Ethyl | 2-isopropyl-1,3-dioxepan-5-yl | H | $\delta$ = 0.90(d), 1.14(t), 1.32(t), 4.30(m) |
| 22 | n-Propyl | Ethyl | 2-isopropyl-1,3-dioxepan-5-yl | H | $n_D^{26}$ = 1.514 |
| 23 | n-Propyl | Ethyl | 3-Tetrahydrothiopyranyl | COOCH$_3$ | $n_D^{22}$ = 1.5431 |
| 24 | Ethyl | 3-Chloroalkyl (trans) | 3-Tetrahydropyranyl | H | $n_D^{22}$ = 1.5480 |
| 25 | Ethyl | 3-Chloroalkyl (trans) | 4-Tetrahydropyranyl | H | 1.1(t),3.4(t), 4.5(d) |
| 26 | n-Propyl | 3-Chloroalkyl (trans) | " | H | $n_D^{19}$ = 1.5407 |
| 27 | Ethyl | 3-Chloroalkyl (trans) | 3-Tetrahydrofuranyl | H | mp. = 50–52° C. |
| 28 | n-Propyl | 3-Chloroalkyl (trans) | " | H | mp. = 55° C. |
| 29 | n-Propyl | 3-Chloroalkyl (trans) | 3-Tetrahydrothiopyranyl | H | $n_D^{22}$ = 1.5669 |
| 30 | " | Methyl | " | H | 0.95(t), 2.9(t), 3.85(s) |
| 31 | " | n-Propyl | " | H | $n_D^{22}$ = 1.5437 |
| 32 | " | Propargyl | " | H | $n_D^{21}$ = 1.5621 |
| 33 | Ethyl | " | " | H | $n_D^{21}$ = 1.5676 |
| 34 | " | n-Propyl | " | H | mp.: 54–56° C. |
| 35 | n-Propyl | Ethyl | " | COOCH$_3$ | $n_D^{22}$ = 1.5431 |
| 36 | " | Allyl | " | COOCH$_3$ | $n_D^{22}$ = 1.5468 |
| 37 | 2-Methyl-propyl | Ethyl | " | H | 0.85(d), 2.9(d), 4.10(t) |
| 38 | 2-Methyl propyl | Allyl | " | H | $n_D^{23}$ = 1.5594 |
| 39 | 2-Methyl-propyl | Methyl | " | H | $n_D^{23}$ = 1.5600 |
| 40 | n-Butyl | Ethyl | " | H | $n_D^{23}$ = 1.5447 |
| 41 | " | Allyl | " | H | $n_D^{23}$ = 1.5500 |
| 42 | n-Propyl | Isopropyl | " | H | 1.3(d) 4.25(pept) |
| 43 | " | Isobutyl | " | H | 0.95(d + t) 2.9(q) 3.8(d) |
| 44 | " | 2-Methyl-2-propen-1-yl | " | H | 4.4(s) 5.05(s) |

The following compounds were also prepared:

| No. | |
|---|---|
| 45 | sodium salt of compound 4 |
| 46 | potassium salt of compound 4 |
| 47 | magnesium salt of compound 4 |
| 48 | calcium salt of compound 4 |
| 49 | tetramethylammonium salt of compound 4 |
| 50 | trimethylbenzylammonium salt of compound 4 |
| 51 | trimethylsulfenium salt of compound 4 |
| 52 | trimethylsulfoxenium salt of compound 4 |
| 53 | aluminum salt of compound 4. |

Application of the conventional active ingredients as herbicides is usually carried out in practice from 10 to 30 days after emergence of the crops, the application rates being from 0.1 to 1 kg/ha of active ingredient. Under these conditions, the grasses (Gramineae) are substantially destroyed.

It is surprising that, for example, sugar cane plants, which belong to the Gramineae family, are not damaged in the method according to the invention, where the active ingredients are applied in amounts of from 1 to 1,000 g of active ingredient per ha from 1 to 15 weeks prior to harvesting.

The application rates can vary within wide limits, for example from 1 to 1,000, in particular from 10 to 1,000, preferably from 20 to 500, g/ha of active ingredient. The total amount used can be applied in a single dose or in two part doses.

According to the invention, the plants are treated from 1 to 15, in particular from 1 to 13, preferably from 1 to 12, weeks prior to harvesting. It may be advantageous to use conventional formulation assistants and possibly a wetting agent.

The Examples which follow illustrate the method according to the invention.

The polarization is the rotation of polarized light in the crude sap of the sugar-containing plants, this rotation being due to the presence of optically active compounds, including sucrose, in the sap.

Sucrose is the content of cane sugar in the crude sap, expressed as a percentage by weight.

Purity is the content of sugar in the constituents dissolved in the crude sap, expressed as a percentage by weight. All values stated in the Examples were determined on the day of harvesting.

EXAMPLE 1

*Saccharum officinarum*, variety CB 4789 Treatment: 5 weeks prior to harvesting (analysis) on first year sugar cane plants

|  | g/ha of active ingredient | Polarization sucrose % | Purity % |
|---|---|---|---|
| Untreated | 0 | 13.6 | 86.7 |
| Compound No. 1 | 300 | 13.9 | 88.3 |
| Comparison* | 900 | 13.4 | 86.2 |

*The comparative agent is the compound of Example VII of European Patent 47,972.

The sugar cane stems harvested representatively by the conventional experimental methods were analyzed in the laboratory according to the known standard guidelines. The result shows an increased sucrose content coupled with higher sap purity. This shows that there is a direct influence which increases the sugar yield.

Compound No. 1 increases the sugar yield compared with untreated pieces as well as with the pieces treated with the comparative active ingredient.

EXAMPLE 2

*Saccharum officinarum*, variety CP 6 3-588

Treatment: 4 weeks prior to harvesting (analysis) on first year sugar cane plants

|  | g/ha of active ingredient | Polarization sucrose % | Purity*** % | Sugar yield, kg of sugar/ tonne of cane |
|---|---|---|---|---|
| Untreated | 0 | 13.0 | 100 | 280.0 = 100 |
| Compound No. 4 | 28 | 14.2 | 100.5 | 110 |
|  | 112 | 14.5 | 101.0 | 112 |
| Comparison* | 56 | 13.2 | 94.2 | 99 |
| Comparison** | 3360 | 14.5 | 99.4 | 111 |

*The comparison is the active ingredient of Example VII of European Patent 47,972
**The comparison is the active ingredient glyphosine [N,N—bis(phosphonomethyl) glycine], cf. U.S. Pat. No. 3,455,675
***After conversion to standard conditions (after-treated = 100)

The experiment was evaluated similarly to Example 1. At both application rates, Compound No. 4 increased the sucrose content as well as the sap purity. The resulting sugar yield was increased by from 10 to 12% compared with untreated pieces. The action is similar to that of the standard, although the latter has to be used in a dose which is from 30 to 120 times higher in order to obtain a satisfactory result.

EXAMPLE 3

*Saccharum officinarum*, variety CP 63-588

Treatment: 8 weeks prior to harvesting (analysis) on first year sugar cane plants

|  | g/ha of active ingredient | Polarization sucrose % | Purity % | Sugar yield, kg of sugar/ tonne of cane |
|---|---|---|---|---|
| Untreated | 28 | 13.4 | 96.5 | 284.9 = 100 |
| Compound No. 4 | 28 | 14.0 | 98.0 | 105 |
|  | 112 | 14.5 | 100.0 | 110 |
| Comparison* | 56 | 13.3 | 94.0 | 98 |
| Comparison** | 3,360 | 14.2 | 98.4 | 107 |

The experiment was evaluated similarly to Example 1. At both application rates, Compound No. 4 increased the sucrose content and the sap purity, giving a sugar yield 5–10% higher than that of the untreated pieces. In this case too, Compound No. 4 is similar to the standard, although the latter has to be applied in an amount which is from 30 to 120 times higher in order to obtain a satisfactory result.

We claim:

1. A method for increasing the sugar content of sugar producing plants, wherein the plants are treated, from 1 to 15 weeks prior to harvesting, with an effective amount of a compound of the formula (I)

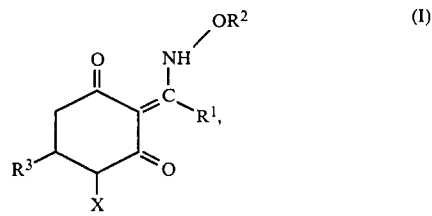

where $R^1$ is alkyl of 1 to 4 carbon atoms, $R^2$ is alkyl of 1 to 4 carbon atoms, unsubstituted or halogen-substituted alkenyl of 3 to 5 carbon atoms or alkynyl of not more than 5 carbon atoms, $R^3$ is a tetrahydropyranyl or a tetrahydrothiopyrnanyl substituent, and can be substituted by alkyl of not more than 3 carbon atoms, and X is H or COO-alkyl, or one of its plant-tolerated salts.

2. A method as defined in claim 1, wherein the plant is sugar cane (*Saccharum officinarum*) or sweet sorghum (*Sorghum saccharatum*).

3. A method as defined in claim 1, wherein the plants are treated with from 1 to 1,000 g/ha of active ingredient.

4. The method of claim 1, wherein $R^3$ is selected from the group consisting of 3-tetrahydrothiopyranal, 3-tetrahydropyranyl and 4-tetrahydropyranal.

5. The method of claim 1, wherein $R^1$ is n-propyl, $R^2$ is ethyl and $R^3$ is 3-tetrahydrothiopyranyl.

6. The method of claim 1, wherein $R^3$ is 4-methyltetrahydropyran-3-yl.

7. The method of claim 3, wherein the plants are treated with from 20 to 500g/ha of active ingredient.

8. The method of claim 1, wherein the plants are treated from 1 to 12 weeks prior to harvesting.

* * * * *